US00PP09738P

United States Patent [19]

Fuess

[11] Patent Number: Plant 9,738

[45] Date of Patent: Dec. 10, 1996

[54] CHRYSANTHEMUM PLANT NAMED 'EMPIRE CROWN JEWEL'

[76] Inventor: Janet S. Fuess, 22 Country Club Dr., New York Mills, N.Y. 13417

[21] Appl. No.: 520,466

[22] Filed: Aug. 25, 1995

[51] Int. Cl.[6] ..... A01H 5/00

[52] U.S. Cl. ..... Plt./74.1

[58] Field of Search ..... Plt./74.1, 82.5, Plt./82.4

[56] References Cited

U.S. PATENT DOCUMENTS

P.P. 6,332 10/1988 VandenBerg ..... Plt./74.1

*Primary Examiner*—Howard J. Locker
*Attorney, Agent, or Firm*—Foley & Lardner

[57] ABSTRACT

A Chrysanthemum plant named Empire Crown Jewel particularly characterized by its flat capitulum form; daisy capitulum type; dark red-purple ray floret color; diameter across face of capitulum of 50 to 55 mm when fully opened; spreading branching pattern; natural season flower date of August 23 to 28 when planting rooted cuttings on June 17 to 18 in Salinas, Calif., and September 25 to October 2 when planting rooted cuttings June 15 to June 22 in Hightstown, N.J.; plant height of 23 to 28 cm when grown in fall under natural daylength with no growth regulators; and durable, uniform performance, with minimal color fading under outside conditions.

3 Drawing Sheets

The present invention comprises a new and distinct cultivar of Chrysanthemum, botanically known as *Dendranthema grandiflora,* and referred to by the cultivar name Empire Crown Jewel.

Empire Crown Jewel, identified as 9866 (W91-5), was originated from a cross made by the inventor Janet S. Fuess in a controlled breeding program in New Hartford, N.Y. in October 1990.

The female parent of Empire Crown Jewel was an unnamed seedling, identified as C87-127, and described as a purple daisy garden mum.

The male parent of Empire Crown Jewel was the cultivar Stardom, disclosed in U.S. Plant Pat. No. 3,530.

Empire Crown Jewel was discovered and selected as one flowering plant within the progeny of the stated cross by Janet S. Fuess in September 1991 in New Hartford, N.Y.

The first act of asexual reproduction of Empire Crown Jewel was accomplished when vegetative cuttings were taken from the initial selection in October 1991 in a controlled environment in New Hartford, N.Y. by Janet S. Fuess.

Horticultural examination of controlled flowerings of successive plantings has shown that the unique combination of characteristics as herein disclosed for Empire Crown Jewel are firmly fixed and are retained through successive generations of asexual reproduction.

Empire Crown Jewel has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Crown Jewel, which, in combination, distinguish this Chrysanthemum as a new and distinct cultivar:

1. Flat capitulum form.
2. Daisy capitulum type.
3. Red-purple ray floret color.
4. Diameter across face of capitulum of 50 to 55 mm when fully opened.

5. Branching pattern is spreading.
6. Natural season flower date of August 23 to 28 when planting rooted cuttings on June 17 and 18 in Salinas, Calif., and September 25 to October 2 when planting rooted cuttings June 15 to June 22 in Hightstown, N.J.
7. Plant height of 23 to 28 cm when grown in fall under natural daylength with no growth regulators.
8. Durable, uniform performance, with minimal color fading under outside conditions.

The accompanying photographic drawings show typical inflorescence and leaf characteristics of Empire Crown Jewel, with the colors being as nearly true as possible with illustrations of this type.

Sheet 1 is a color photograph of Empire Crown Jewel grown in natural season outside conditions in Salinas, Calif.

Sheet 2 is a black and white photograph of three views of the inflorescence of Empire Crown Jewel.

Sheet 3 is a black and white photograph showing the upper and under sides of the leaves of Empire Crown Jewel at 3 stages of development (mature, intermediate and immature). In sheets 2 and 3 a measuring tape in centimeters has been added.

Of the commercial cultivars known to the inventor, the most similar in comparison to Empire Crown Jewel is the cultivar identified as Kimberly, disclosed in U.S. Plant Pat. No. 9,026. Reference is made to attached Chart A, which compares certain characteristics of Empire Crown Jewel to the same characteristics of Kimberly.

Similar traits are capitulum form and type. Empire Crown Jewel has a much darker ray floret color, a slightly larger diameter of capitulum, a more spreading branching pattern, an earlier natural season flower date, and a shorter plant height when compared with Kimberly.

In the following description color references are made to The Royal Horticultural Society Colour Chart. The color values were determined on plant material grown as a pinched garden mum grown outdoors in Salinas, Calif. on Aug. 23, 1994.

Classification:

*Botanical.*—*Dendranthema grandiflora* cv Empire Crown Jewel.

*Commercial.*—Flat daisy garden mum.

INFLORESCENCE

A. Capitulum:
*Form.*—Flat
*Type.*—Daisy.
*Diameter across face.*—50 to 55 mm when fully opened.

B. Corolla of ray florets:
*Color (general tonality from a distance of three meters).*—Dark red-purple.
*Color (upper surface).*—70A.
*Color (Under surface).*—70D, overlaid with 70A.
*Shape.*—Flat, straight, ray floret tip is round.

C. Corolla of disc florets:
*Color (mature).*—15B.
*Color (immature).*—6B tinged with 151D.

D. Reproductive organs:
*Androecium.*—Present on disc florets only; moderate pollen.
*Gynoecium.*—Present on both ray and disc florets.

PLANT

A. General appearance:
*Height.*—23 to 28 cm when grown in fall under natural daylength with no growth regulators.
*Branching pattern.*—Spreading.

B. Foliage:

*Color (upper surface).*—147A.
*Color (under surface).*—147B.
*Shape.*—Very deeply lobed.

CHART A

COMPARISONS MADE OF PLANTS GROWN UNDER NATURAL SEASON OUTDOOR CONDITIONS IN SALINAS, CALIFORNIA AND IN HIGHTSTOWN, NEW JERSEY

| Characteristic | Empire Crown Jewel | Kimberly |
|---|---|---|
| Ray floret color | Red-purple | Light purple |
| Capitulum form and type | Flat<br>Daisy | Flat<br>Daisy |
| Diameter across face of capitulum | 50 to 55 mm | 47 to 52 mm |
| Branching pattern | Spreading | Semi-spreading |
| Natural season flower date: | | |
| in Salinas, CA | Aug 23 to 28 | Sep 2 to 7 |
| in Hightstown, NJ | Sep 25 to Oct 2 | Oct 5 to 17 |
| Plant height: | 23 to 28 cm | 30 to 36 cm |

I claim:

1. A new and distinct Chrysanthemum plant named Empire Crown Jewel, as described and illustrated.

* * * * *

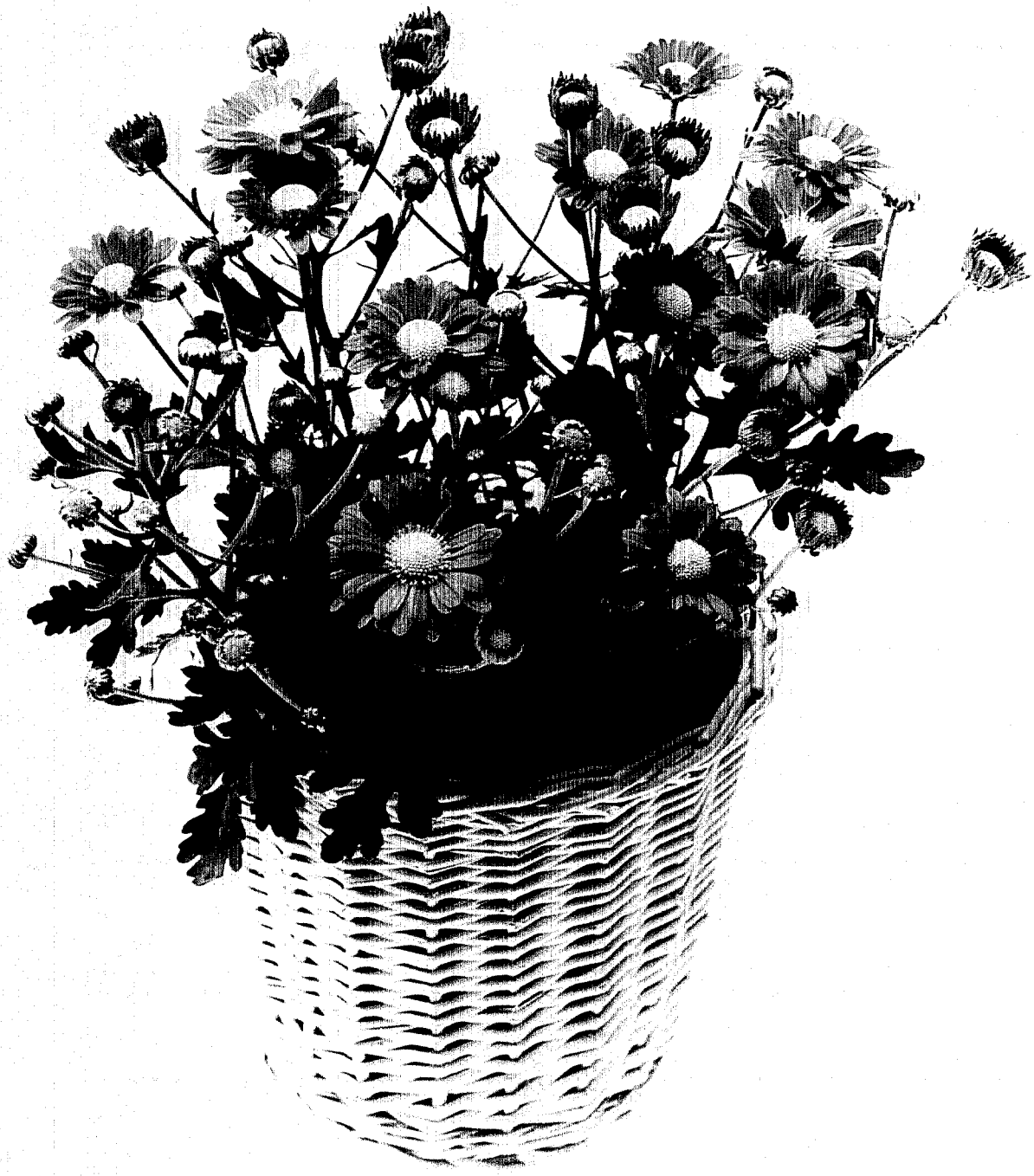

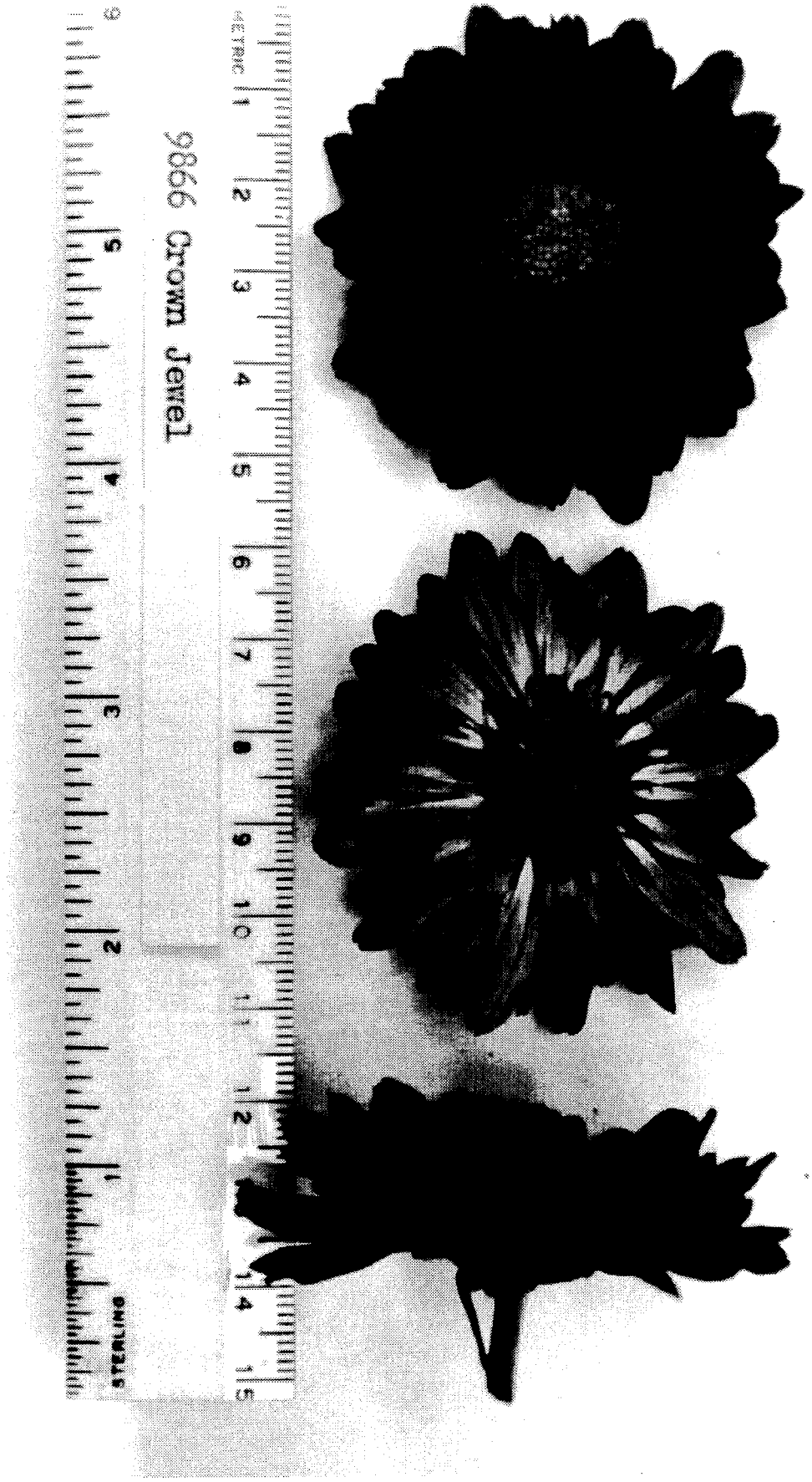
9866 Crown Jewel

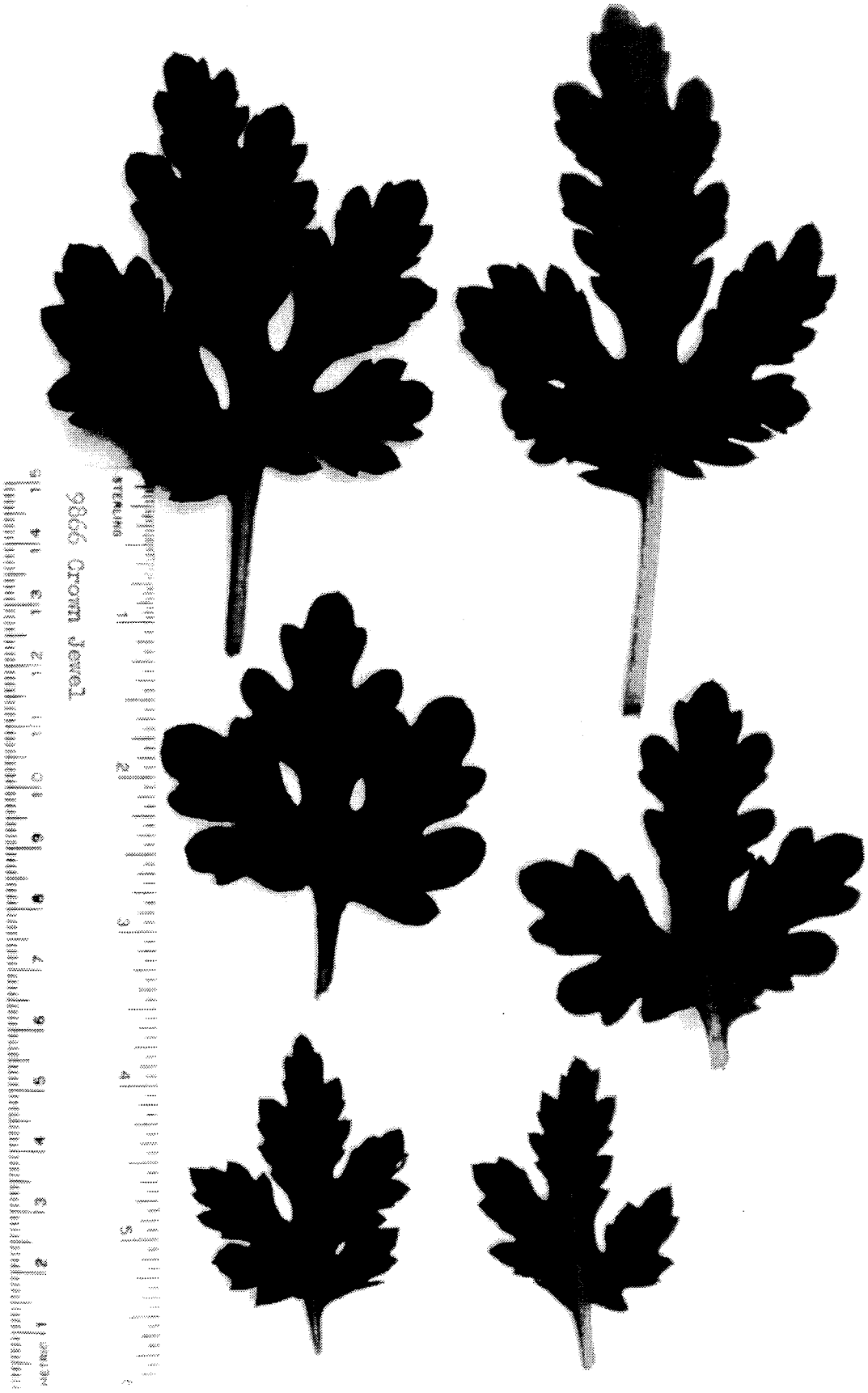
9866 Crown Jewel